US010960110B2

(12) United States Patent
Xie (10) Patent No.: US 10,960,110 B2
(45) Date of Patent: Mar. 30, 2021

(54) IRON-BASED BIODEGRADABLE METALS FOR IMPLANTABLE MEDICAL DEVICES

(71) Applicant: Jian Xie, Valencia, CA (US)

(72) Inventor: Jian Xie, Valencia, CA (US)

(73) Assignee: Jian Xie, Valencia, CA (US)

( * ) Notice: Subject to any disclaimer, the term of this patent is extended or adjusted under 35 U.S.C. 154(b) by 350 days.

(21) Appl. No.: 16/106,971

(22) Filed: Aug. 21, 2018

(65) Prior Publication Data
US 2020/0061251 A1    Feb. 27, 2020

(51) Int. Cl.
| | | |
|---|---|---|
| *A61L 31/02* | (2006.01) | |
| *A61L 31/12* | (2006.01) | |
| *A61L 27/42* | (2006.01) | |
| *A61L 27/58* | (2006.01) | |
| *A61L 27/04* | (2006.01) | |
| *A61L 27/34* | (2006.01) | |
| *A61L 27/54* | (2006.01) | |
| *A61L 31/14* | (2006.01) | |
| *A61L 31/16* | (2006.01) | |
| *A61L 31/08* | (2006.01) | |

(52) U.S. Cl.
CPC .......... *A61L 31/022* (2013.01); *A61L 27/042* (2013.01); *A61L 27/34* (2013.01); *A61L 27/427* (2013.01); *A61L 27/54* (2013.01); *A61L 27/58* (2013.01); *A61L 31/08* (2013.01); *A61L 31/124* (2013.01); *A61L 31/148* (2013.01); *A61L 31/16* (2013.01); *A61L 2300/416* (2013.01); *A61L 2300/604* (2013.01); *A61L 2420/04* (2013.01)

(58) Field of Classification Search
None
See application file for complete search history.

(56) References Cited

U.S. PATENT DOCUMENTS

| | | | |
|---|---|---|---|
| 8,986,369 B2* | 3/2015 | Steckel | A61L 31/022 623/1.38 |
| 10,052,405 B2* | 8/2018 | Koo | A61L 27/48 |
| 10,085,860 B2* | 10/2018 | Steckel | A61L 27/58 |
| 10,689,773 B2* | 6/2020 | Whitaker | C25D 5/10 |
| 2006/0147491 A1* | 7/2006 | DeWitt | A61L 31/10 424/426 |
| 2008/0097575 A1* | 4/2008 | Cottone | A61L 31/047 623/1.13 |
| 2009/0081313 A1* | 3/2009 | Aghion | A61L 27/58 424/641 |
| 2011/0251669 A1* | 10/2011 | Heublein | A61L 31/148 623/1.15 |
| 2011/0318219 A1* | 12/2011 | Bayer | C22C 38/60 420/83 |

(Continued)

*Primary Examiner* — Kevin R Kruer (57) ABSTRACT

Iron-based biodegradable metals and the method of fabricating are disclosed. The iron-based biodegradable metals, which have an accelerated degradation rate and a yield strength similar to stainless steel, comprises a composite structure of multiple iron layers separated by thin alloying metallic layers. The composite structure are built layer by layer using additive manufacturing technologies. The iron-based biodegradable metals can be fabricated into a small diameter tube for laser cutting into implantable bare metal stents or drug eluting stents with biodegradable polymer coating. The iron-based biodegradable metals can be fabricated and/or machined into orthopedic implants.

11 Claims, 7 Drawing Sheets

(56) References Cited

U.S. PATENT DOCUMENTS

| | | | |
|---|---|---|---|
| 2012/0035740 A1* | 2/2012 | Koo | A61L 27/427 623/23.55 |
| 2013/0066417 A1* | 3/2013 | Huang | C23C 14/48 623/1.38 |
| 2013/0243699 A1* | 9/2013 | Wang | C22C 38/002 424/9.32 |
| 2014/0097277 A1* | 4/2014 | Kumta | A61L 31/148 241/15 |
| 2016/0100926 A1* | 4/2016 | Bayon | A61L 27/24 606/151 |
| 2016/0262915 A1* | 9/2016 | Mangiardi | A61L 31/022 |
| 2019/0269532 A1* | 9/2019 | Mangiardi | A61F 2/915 |
| 2020/0000973 A1* | 1/2020 | Kumta | A61L 31/148 |
| 2020/0061251 A1* | 2/2020 | Xie | A61L 27/427 |
| 2020/0179084 A1* | 6/2020 | Manuel | A61L 27/047 |
| 2020/0232079 A1* | 7/2020 | Disegi | C22C 33/0221 |

\* cited by examiner

IRON-BASED BIODEGRADABLE METALS FOR IMPLANTABLE MEDICAL DEVICES

FIELD OF INVENTION

The present disclosure relates to iron-based biodegradable metals and their applications to implantable medical devices such as cardiovascular stents and orthopedic implants.

BACKGROUND

Medical implants are mostly made from inert biocompatible metals such as titanium, stainless steel and cobalt-chromium alloys due to excellent biocompatibility, corrosion resistance and mechanical properties. These inert metals are intentionally designed to remain in the human body once they are implanted. In many medical cases, only a temporary supporting function in the human body is needed until the tissue healing is completed. For example, the metallic plates and screws to fix the broken bones may be required to be removed by a secondary surgery after the broken bones are fully healed. The other example is the drug-eluting stents (DES) made of 316L stainless steel, which is designed to permanently remain in the blood vessel. The stents are small mesh-like scaffolds to provide mechanical support to the diseased blood vessels from preventing elastic arterial recoil following the angioplasty procedure. After a predetermined period of time of scaffolding to the vessels, typically about 6 to 12 month, the diseased vessels shall be remodeled and healed to keep it open for blood flow and the scaffolding is no longer needed. Use of the permanent inert stent to fulfill the temporary supporting function has been clinically proved to cause several complications including very late thrombosis, chronic inflammation, long-term endothelial dysfunction, in-stent restenosis, permanent physical irritation, long term anti-platelet therapy, inability to adapt to the growth of young patients, and distortion of diagnostic imaging.

It is a logic approach to use biodegradable biomaterials for such a temporary medical need: the medical implants shall be fully degraded after tissue healing is completed and then the surrounding tissues shall not be adversely interfered by the medical implants any more in the human body.

Two categories of biodegradable biomaterials are extensively investigated in the last two decades: Synthetic polymeric biomaterials such as Poly-L-Lactic (PLLA), Polyglycolic acid (PGA) and tyrosine polycarbonate, and metallic biomaterials such as magnesium, iron and zinc. The major criteria to select a biomaterial for such a temporary medical need is its biodegradation rate. The initial study indicated that the polymeric biomaterials had a degradation time from 6 to 48 months which fell into the range of the temporary medical need and considerable efforts were made on the development of polymeric biomaterials for biodegradable medical implants in the last two decades, particularly biodegradable stents or scaffolds to treat coronary artery diseases. The biodegradable polymers have mechanical properties considerably lower than metals, and the supporting efficiency of the polymeric stents or scaffolds is not as good as current metallic stents currently in the market. U.S. Food and Drug Administration (FDA) approved first and only polymeric biodegradable coronary stent made of PLLA from Abbot (Absorb BVS) in 2016 based on one-year clinical data. However, FDA issued a warning letter to health care providers in 2017 that the interim two-year clinical results showed an increased rate of major adverse cardiac events. Later in 2017, Abbott stopped global sales of the approved polymeric PLLA stent, and another leading medical device giant in the US was reported to scrap its polymeric biodegradable stent program based on the rival discouraging clinical results.

Biocompatible metals have been used for coronary stents since introduction of first-generation stents in the market and still dominate the market due to the proved long-term clinical safety in addition to the excellent biocompatibility and mechanical properties to support the diseased arterial vessels. However, the major challenge in using biocompatible metals as a scaffold for the temporary medical need is that all commercially available biodegradable metals (iron, magnesium, zinc and their alloys) do not meet the requirements of the degradation rate and mechanical properties simultaneously. The commercially available biodegradable metals either degrade too fast (such as magnesium) or too slow (such as iron) or poor mechanical properties (such as zinc).

Recent advances in biodegradable metals in last decade demonstrated the potential to use the biodegradable metals to treat the heart diseases and broken bones. The medical implants made from biodegradable metals are significantly stronger than the polymer counterparts, and the degraded metal particles are fully dissolvable in the body fluids. Phagocytic cells can dissolve the excess amount of degraded metal particles or corrosive products. The degradation of biodegradable metals in physiological environment takes places through a series of anodic and cathodic reactions. The biodegradable metals potentially used for medical implants include magnesium, iron, zinc and their alloys.

Magnesium alloys were first used as orthopedic implants, but they have been receiving much attentions as a cardiovascular stent in the last decade. The magnesium alloys, AE21 (97% Mg, 2% Al, and 1% rare earth) and WE43 (>85% Mg, <5% Y, <5% of Zr and <5% of rare earth), were investigated as the cardiovascular stent material. The biodegradation of magnesium alloys involves hydrolysis of magnesium chloride in physiological environment, decomposing to the hydrogen gas and magnesium hydroxide. However, biodegradation rate of magnesium and alloys is too fast and it is typically degraded within about one month. It was reported in U.S. Pat. No. 9,468,704B2 that a new magnesium alloy with significant amount of rare-earth elements was developed to extend the degradation time up to three months. Multiple approaches such as surface modification, coating, alloying and fabrication processes etc. have been taken to slow down the degradation, further development is needed in order to meet the minimum requirement of six months for the cardiovascular stent application.

Zinc is an essential element in the human body and is a component of more than 300 enzymes and greater number of other proteins. As zinc has standard electrode potential of $-0.762V$ falling between magnesium ($-2.372V$) and iron ($-0.444V$), it exhibits a moderate degradation rate: significantly slower than Mg but faster than Fe, which make zinc a candidate for the biodegradable implants in recent years. One of the limitations of pure zinc is low mechanical strength (Ultimate Tensile Strength about 30 MPa) and plasticity (elongation<1%). The efforts are being made to improve zinc's mechanical properties by adding alloying elements and modifying the microstructures, while maintaining its biocompatibility and biodegradation property. The challenge is that the zinc-based materials have not yet been reproducibly shown to posse both the mechanical and biodegradation properties required for the temporary medical implants. As a relatively new biodegradable metal, the long term in vivo biodegradation mechanism is not fully understood and more works are being done to confirm their suitability as biodegradable metals.

Iron is also an essential element in the human body with a high content in blood (447 mg/L) and high allowable daily intake (10 to 17 mg/day) and the iron stent weight about 40 mg make body systemic iron toxicity less likely. The excellent mechanical properties of iron provide a strong radial strength to support the blood vessels after implantation. It has been reported that iron was oxidized to ferrous iron and ferric iron by the phagocytosis of nearby tissues, and the ferrous iron reduced the proliferation of smooth muscle cells in vitro tissue culture so as to suppress the formation of neointimal in the blood vessels. However, the in vivo degradation rate is extremely slow and the iron stents may take up to 10 years to fully degrade in the human body. Significant efforts were made in recent years to accelerate iron biodegradation by adding alloying elements, surface modification, changes in microstructures, and use of non-traditional fabrication processes such as powder metallurgy, electroforming and inkjet 3D-printing.

Manganese (Mn) is an alloying element to add into iron (Fe—30% Mn) to accelerate the degradation of the iron-based metals. Adding of 6% of Si (Fe—30% Mn—6% Si) can have a shape memory effect while a recovery ratio 53.7% could be reached at the total strain of 3% and the exact pre-strain of 2.73%. As forged Fe—30% Mn—1% C alloy showed a significant increase in ultimate strength to 1010 MPa and elongation to 88%, respectively. Both Fe—30% Mn—6% Si and Fe—30% Mn—1% C alloys exhibited an enhanced biodegradation behavior. Adding 1% Pd (Fe—10% Mn—1% Pd) improved the tensile strength but reduced the ductility, while a degradation rate was higher than that of low carbon steel. However, it was found that immersion test results of Fe—Mn alloys had a degradation rate slightly slower than those of pure iron. The effect of eight alloying elements (Mn, Co, Al, W, Sn, B, C, and S) at 3% by weight on the degradation and biocompatibility of iron-based metals was investigated and it was found that the acceleration in biodegradation rate is limited.

Powder metallurgy Fe—Mn, Fe—C, Fe—P, Fe—B, and Fe—Ag alloy was found to have an increased degradation rate due to process porosity inside. Electroformed pure iron showed a faster in-vitro degradation than casting iron due to a fine grain size with a grain size about 5 μm. Nanocrystalline pure Fe prepared by the equal channel angular pressing (ECAP) technique exhibited superior strength but significant decrease in degradation rate. Fe—30% Mn scaffolds fabricated by inkjet 3D printing with a porosity of 36.3% demonstrated that tensile property was close to the natural bone and was appropriate for low load-bearing applications. Electrochemical corrosion tests indicated the 3D printed Fe—30% Mn could be degraded at a higher rate than pure iron.

In order to accelerate the degradation of pure iron, a variety of secondary phases were added into the iron matrix to generate micro-galvanic corrosion between iron matrix (anode) and secondary phases (cathode). Tungsten (W) and carbon nanotubes (CNTs) are conductive and act as superior cathodes. Three types of iron-based composites (Fe—W, Fe—CNT, and Fe—$Fe_2O_3$) were prepared by spark plasma sintering technique and it was found the ultimate compressive strength was significantly improved without scarifying the ductility. The addition of Tungsten or $Fe_2O_3$ only slightly enhanced the degradation rate, while the addition of CNT increases obviously, about 2 times higher than pure iron in degradation rate.

Surface modification on pure iron substrates has also been tried, including lanthanum ions implantation, deposited Fe—O films, zinc ion implantation, plasma nitriding, and calcium zinc phosphate coating. The surface modification methods are able to effectively improve the biocompatibility of pure iron and improve the degradation rate.

Iron-based biodegradable material is one of the biodegradable metallic materials that are most widely investigated and has excellent mechanical properties and biocompatibility. Despite the progresses in accelerating the biodegradation rate, there is still a big gap in degradation rate for clinical applications and further development with a higher degradation rate is needed.

The present inventions describe iron-based biodegradable metals which have a significant higher biodegradation rate than pure iron and pure zinc, while maintaining the good biocompatibility and mechanical properties similar to 316L stainless steel. The degradation rate of the iron-based biodegradable metals in the present inventions can be controlled by the changes in the macro structures, alloying elements/second phases and their amounts to meet the needs of various types of medical implant applications. The iron-based biodegradable metals can be used to fabricate orthopedic implants and cardiovascular or peripheral stents.

SUMMARY

Iron-based biodegradable metals in accordance with one at least one of the present inventions include a composite structure of multiple iron layers separated by thin alloying metal layers, while the iron layers comprise large columnar iron grains and/or small equiaxed iron grains, and the alloying elements in the alloying layers include zinc or magnesium or their combination with a total amount less than 0.5% by weight.

The iron-based biodegradable metals with composite structure of multiple iron layers can be built layer by layer by additive manufacturing (AM) technologies such as laser selective sintering, electron beam selective melting, electroforming, physical vapor deposition, electroplating, or friction stir processing.

The iron-based biodegradable metals according to the present disclosure have a degradation rate greater than that of pure iron and pure zinc, but lower than that of fast-degraded magnesium. The iron-based biodegradable metals are ductile and have a yield strength ranging from 150 to 600 MPa with good ductility.

The iron-based biodegradable metals in the present inventions can be built into various forms including small diameter tubes, plates or foils, screws etc. to be manufactured as implantable medical devices. The small diameter tube has a composite structure of multiple circular iron layers separated by a thin circular alloying metallic layers, and it can be laser cut into cardiovascular or peripheral stents to be deployed into diseased blood vessels to keep them open and restore the flow of blood. The implanted stents shall be degraded, absorbed and excreted over a predetermined period of time after fully healing of the blood vessels. In addition to that, the biodegradable metals in the present inventions can be used to fabricate orthopedic implants such as bone plates and screws to fix and repair the broken bones. The implanted bone plates and screws shall be gradually degraded after bone healing and thus the secondary surgery to remove the orthopedic implants is avoided.

The features of the present inventions shall become apparent as the inventions become better understood by reference to the following detailed description when considered in conjunction with the accompanying drawings.

BRIEF DESCRIPTION OF THE DRAWINGS

Detailed descriptions of the exemplary embodiments shall be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the invention.

The present inventions are iron-based biodegradable metals, which can be used to fabricate implantable medical devices, particularly orthopedic implants to eliminate secondary surgery of removing them after healing and implantable stents in arterial vessels to avoid the complications including very late thrombosis and chronic inflammation. The implantable medical devices made by the iron-based biodegradable metals in the inventions shall be degraded, absorbed and excreted over a predetermined period of time in the human body.

The iron-based biodegradable metals according to the present disclosure have a degradation rate greater than that of pure iron and pure zinc, but lower than fast-degraded magnesium in a biological environment. The iron-based biodegradable metals are ductile and have a yield strength ranging from 150 to 600 MPa, depending the structure, amount of alloying elements, and heat treatment processes.

Figure 1:
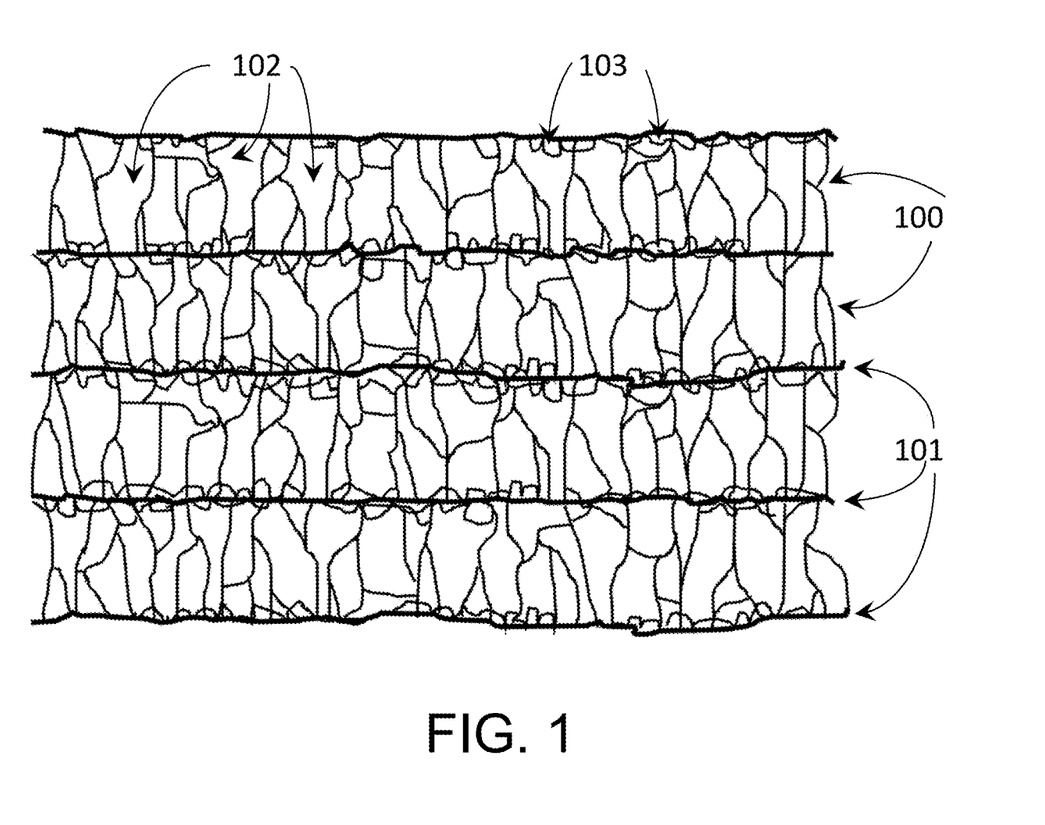
FIG. 1 is a cross section view of the iron-based biodegradable metals showing a composite structure, while the iron layers are separated by thin alloying metallic layers and the iron layers comprise large columnar grains and small equiaxed grains.

The iron-based biodegradable metals in the present inventions have a composite structure instead of a homogeneous structure observed in most metals. A cross section of the exemplary iron-based biodegradable metals is illustrated in FIG. 1. The iron-based biodegradable metals in present invention have a composite structure of multiple iron layers 100 which are separated by the thin alloying metallic layers 101. The iron layers 100 consist of two types of iron grains, large columnar iron grains 102 and small equiaxed iron grains 103, in which the small equiaxed iron grains 103 are near the thin alloying metallic layer 101 as the grains nucleation starts from the alloying metallic layer 101. The iron layers 100 can comprise only large columnar iron grains or small equiaxed iron grains 103 in certain conditions of heat treatment and the alloying amounts in the alloying metallic layer 101. The amount of the small equiaxed grain is one of the factors affecting the degradation rate of the biodegradable metals in the present invention. Grain boundaries 104 can be observed at the interface of two or multiple iron grains in the iron layers 100.

By way of example, but not limitation, the iron layers 100 have a thickness of 5 to 50 μm in most cases but the thickness of the iron layers could be up to 1 mm depending on a specific medical implant application. For a fixed size biodegradable metal, more layers can be achieved by reducing the thickness of iron layers 100. For example, a piece of biodegradable metal with a total thickness of 100 μm consists of five iron layers 100 separated by four thin alloying metallic layers 101 at the iron layer thickness of about 20 μm; It consists of ten iron layers 100 separated by nine thin alloying metallic layers 101 at the iron layer thickness of about 10 μm.

The outer surface of the biodegradable metals can be either an iron layer 100 or an alloying metallic layer 101. The iron layer or alloying metallic layer on the outer surface can have a thickness different from the layers inside the biodegradable metals in the present inventions.

The thickness of every iron layer 100 in the biodegradable metals in the present inventions can be either identical or different. The thickness of every iron layer can vary in order to achieve the desired degradation rate and mechanical properties. For example, the outer iron layer of the biodegradable metals could have a thickness of 10 μm, and adjacent iron layer could have a thickness of 20 μm, and the next iron layer could be 15 μm. In general, the thickness of every iron layer 100 could be totally different from others in the biodegradable metals to meet a specific medical need.

The iron layers 100 can be built layer by layer by additive manufacturing (AM) technologies, including but not limited to, laser selective sintering, electron beam selective melting, electroforming, and friction stir processing.

An exemplary selective laser sintering uses a continuous wave fiber laser with a wavelength of 1.07 μm to scan a layer of fine pure iron powder evenly distributed onto a substrate. A small amount of second-phase particles or other alloying element powder can be added into the iron powder. The substrate is fastened to an indexing table that moves in the vertical (Z) axis. The laser beam is directed in the X and Y directions with two high frequency scanning mirrors. Laser scanning to partially melt the iron powder layer takes place in a chamber with a controlled inert environment. The chamber is filled with a mixed inert gas of 75% argon and 25% helium, and the content of moisture and oxygen is controlled below 100 ppm (part per million). Once the laser scanning on one layer is complete, the indexing table moves down for a new powder layer comprising alloying elements evenly distributed on the previously-melted iron layer 100 for next laser scanning of the iron layer 100 or alloying metallic layer 101. The process is repeated layer after layer until the part is complete.

The iron layers 100 are separated by the alloying metallic layers 101. The alloying metallic layers 101 are much thinner than the iron layers 100 with a thickness from 0.01 μm to 2 μm. The alloying layers 101 have different alloying elements from the iron layers 100. By way of example, but not limitation, the alloying elements in the alloying layers 101 include zinc or magnesium or their combination. The total amount of the alloying elements in the biodegradable metals is less than 0.5% by weight. The thin alloying metallic layers 101 can be deposited on the iron layers 100 by, but not limited to, physical vapor deposition (PVD) including sputtering and evaporation deposition processes, laser selective sintering, electron beam selective melting, or electroplating.

The alloying elements (zinc or magnesium) in the alloying metallic layers 101 can react with the iron layers 100 at the interface to form intermetallic phases or supersaturated solid solution at certain process conditions, for example, Delta $\delta$ phase ($FeZn_{10}$), Gamma $\Gamma$ phase ($Fe_3Zn_{10}$), and Gamma one $\Gamma_1$ phase ($Fe_5Zn_{21}$) for zinc element; or magnesium supersaturated in the body centered cubic (bcc) crystallographic phase of Alpha $\alpha$ phase iron due to the excess energy of coherent interfaces in the Fe—Mg nanocomposite.

Additionally, there may be a very small amount of second-phase particles of the alloy oxides in the alloying layers 101. Particularly, the second-phases particles of the oxides include, but not limited to, mainly ferric oxides ($Fe_2O_3$) and ferrous oxides (FeO, $Fe_3O_4$).

Figure 2:
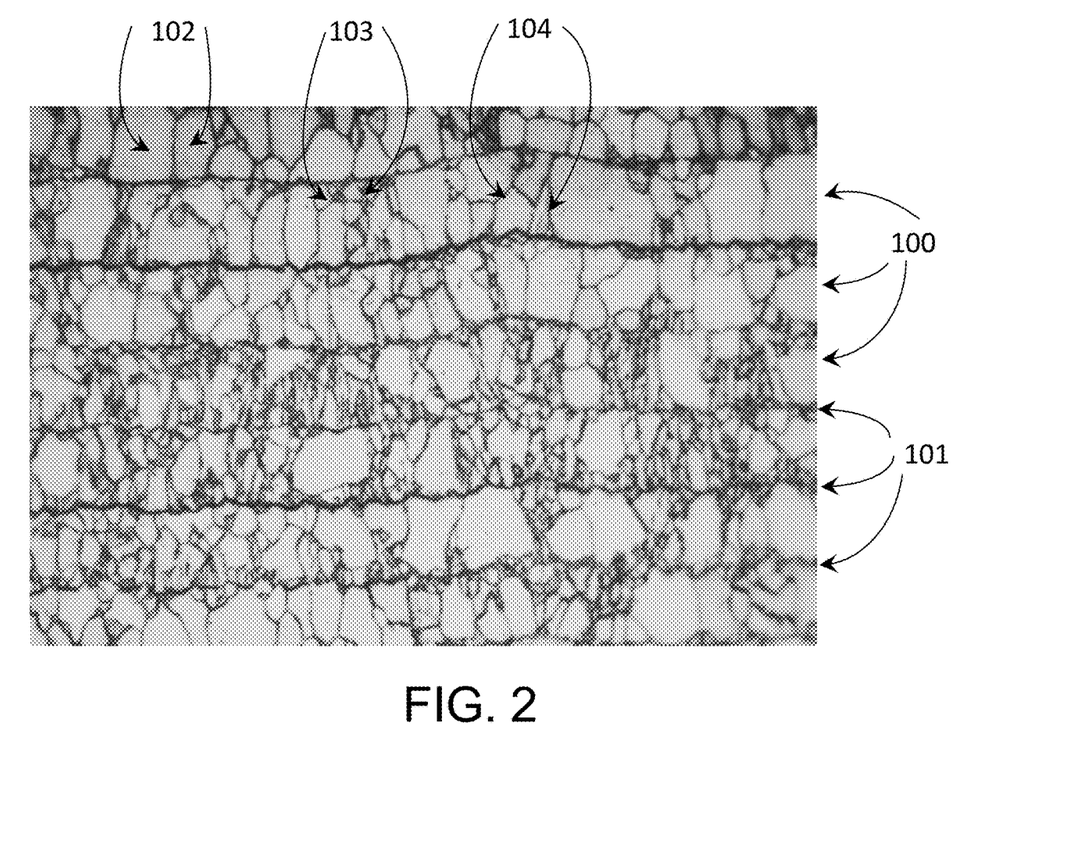
FIG. 2 is a photo of cross section view of the iron-based biodegradable metals at a magnification of 1000 times, showing the iron layers separated by thin alloying metallic layers, and large columnar grains and small equiaxed grains in the iron layers.

A photo of cross section view of the exemplary biodegradable metals at a magnification of 1000 times is shown in FIG. 2, where the iron layers 100 and alloying metallic layers 101 are clearly observed. The iron layers 100 consists of a number of iron grains, including the large columnar iron grains 102 and small equiaxed iron grains 103. The grain boundaries 104 are also observed.

The grain boundaries 104 may consist of a very small amount of second-phase particales of oxides, including but not limited to, ferric oxides ($Fe_2O_3$) and ferrous oxides (FeO, $Fe_3O_4$).

Proper heat treatment on the iron-based biodegradable metals or the implantable medical devices made from the biodegradable metals is needed to achieve desired mechanical properties.

Figure 3:
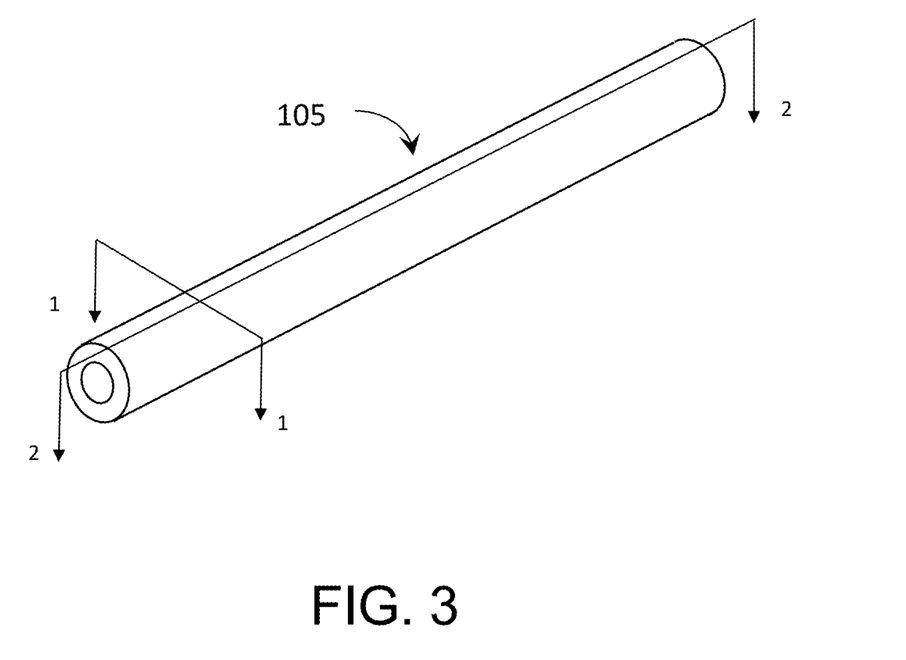
FIG. 3 is a small diameter tube made by the iron-based biodegradable metals.

The biodegradable metals in the present inventions can be built into in various forms including, but not limited to, small diameter tubes, plates or foils, screws used for implantable medical devices. By way of example, but not limitation, the small diameter tubes can be fabricated at an outer diameter of 1.20 mm, 1.40 mm, 1.60 mm, 1.80 mm, 1.90 mm, 2.00 mm, 2.20 mm, 2.40 mm, 3.00 mm, 5.00 mm, and a wall thickness ranging from 0.04 to 0.25 mm. The length of the tubes can be up to 0.5 m depending on the equipment used to build the tubes. An exemplary small diameter tube 105 is illustrated in FIG. 3.

Figure 4:
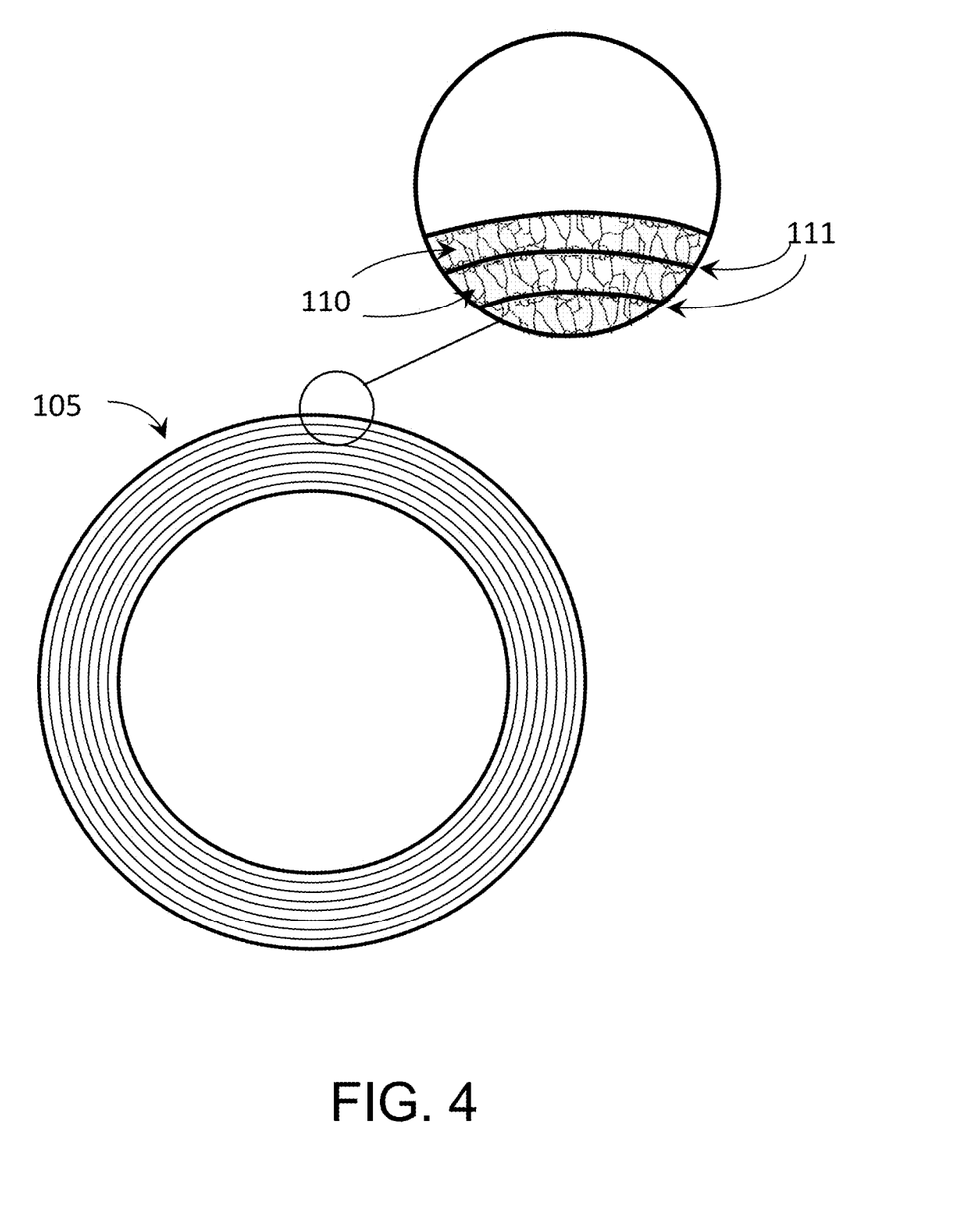
FIG. 4 is a cross section view of a small diameter tube taken along line 1-1 in FIG. 3, showing the circular iron layers separated by circular thin alloying metallic layers.

A cross section view of the exemplary small diameter tube 105 taken along line 1-1 is illustrated in FIG. 4. The small diameter tube 105 has a composite structure of multiple circular iron layers 110 separated by the circular thin alloying metallic layers 111 in the radial direction. The thickness of the circular iron layers 110 is in the range of 5 to 50 μm while it is 0.01 to 2 μm for alloying metallic layers 111.

By way of example, but not limitation, the alloying elements in the alloying layers 111 include zinc or magnesium or their combination. The total amount of the alloying elements in the iron-based biodegradable metals is less than 0.5% by weight. Additionally, there may be a small amount of second-phase particles of the alloy oxides in the alloying layers 111 and grain boundaries. Particularly, the second-phases particles of the oxides include, but not limited to, mainly ferric oxides ($Fe_2O_3$) and ferrous oxides (FeO, $Fe_3O_4$).

The outer surface of the exemplary small diameter tube 105 can be either an iron layer 110 or an alloying metallic layer 111. Similarly, the inner surface of the exemplary small diameter tube 105 can be either an iron layer 110 or an alloying metallic layer 111.

Figure 5:
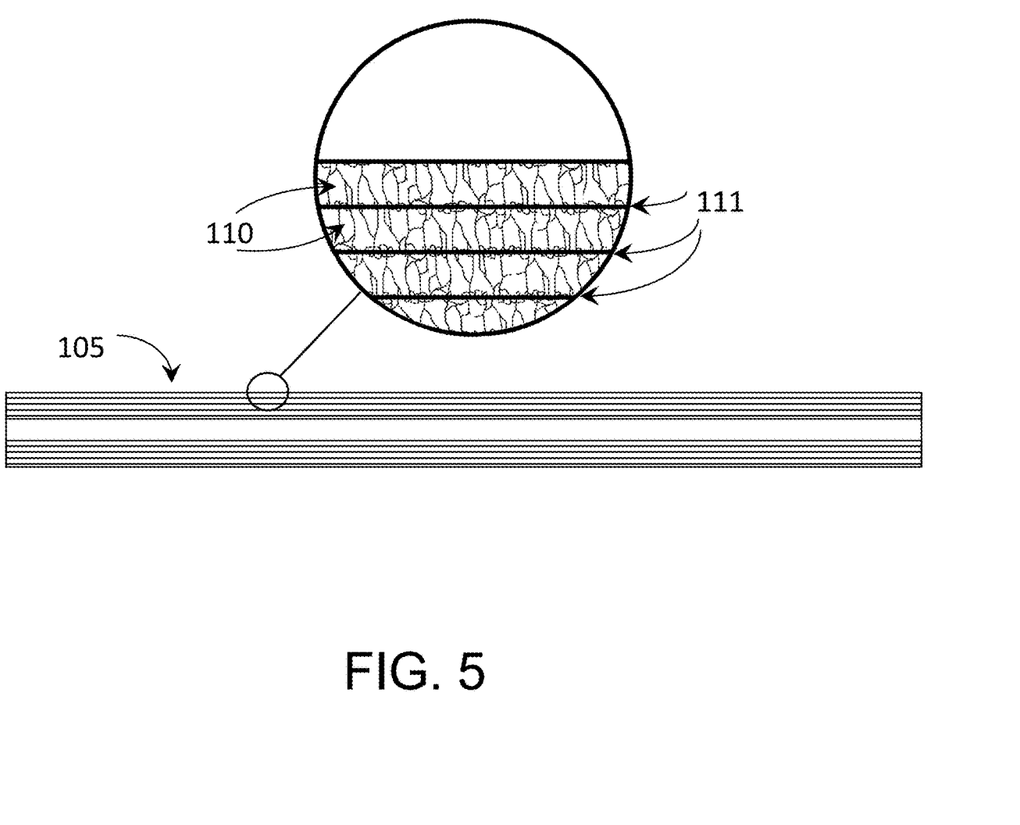
FIG. 5 is a cross section view of a small diameter tube taken along line 2-2 in FIG. 3, showing the circular iron layers separated by circular thin alloying metallic layers.

A cross-section view of the exemplary small diameter tube 105 taken along line 2-2 is illustrated in FIG. 5. This cross-section view shows the composite structure of multiple circular iron layers 110 separated by the circular alloying metallic layers 111 in the longitudinal direction of the exemplary small diameter tube 105. The circular iron layers and thin alloying layers can be built by additive manufacturing technologies such as laser selective sintering, electron beam selective melting, electroforming, physical vapor deposition, electroplating, friction stir processing or combination of above-mentioned processes.

The thickness of every iron layer 110 in FIGS. 4 and 5 can be either identical or different in the radial direction of the exemplary small diameter tube 105. Similarly, the thickness of every alloying metallic layer 111 in the small diameter tube 105 may be either identical or slightly different in the radial direction.

The exemplary small diameter tube 105 in the present inventions can be used to fabricate implantable medical devices. By way of example, but not limitation, the exemplary small tubes 105 can be laser cut into a stent 106 to be deployed into diseased blood vessels to keep them open. The implanted stents restore the flow of blood or other fluids in the human body. There is a wide variety of stents used for different purposes, from expandable coronary, vascular and biliary stents, to the stents used to allow the flow of urine between kidney and bladder. Lasers used to cut the small diameter tube include, but not limited to, fiber lasers, pulsed Nd:YAG, femtosecond lasers, or continuous wave lasers. An exemplary stent made by laser cutting the biodegradable metal tube 105 is illustrated in FIG. 6.

Figure 6:
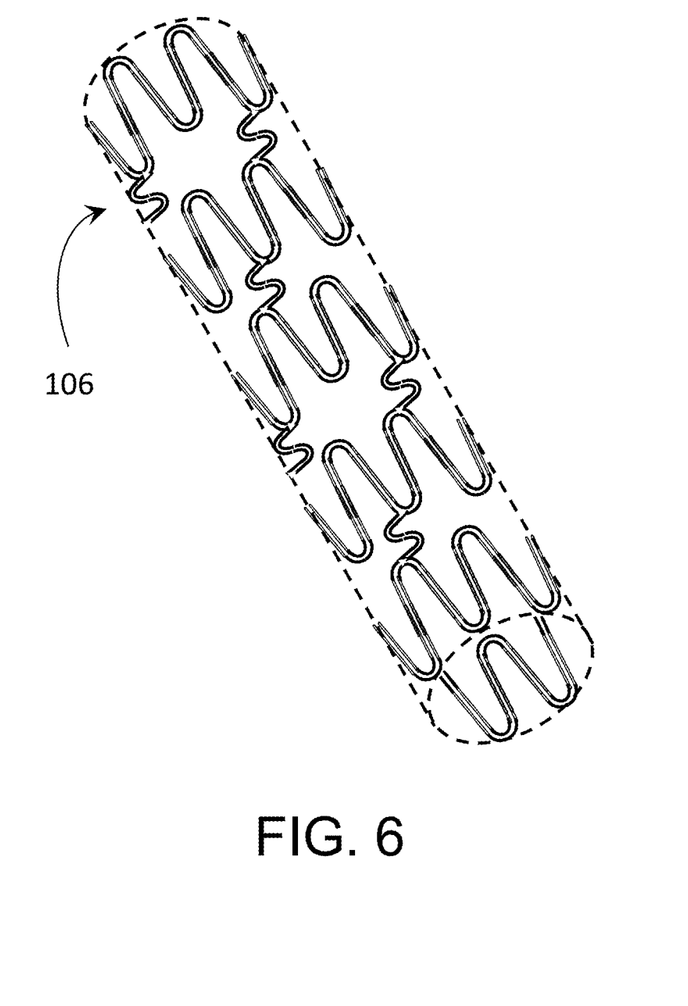
FIG. 6 is a top view of a stent cut by lasers. It can be a bare metal stent or a strut for a drug eluting stent.

By way of example, but not limitation, the exemplary stent 106 in FIG. 6 can be used as a bare metal stent (BMS), or polymer-free stent, or a biodegradable strut of a drug eluting stent (DES) which comprises a biodegradable polymer coating on the strut and a drug added into the polymer coating. The biodegradable polymer coating includes, but not limited to, polyglycolic acid (PGA) and polylactic acid (PLA, also known as PLLA). A certain amount of an antiproliferative drug, for example, sirolimus, paclitaxel, biolimus, and everolimus, are added into the biodegradable polymer coating to reduce neointimal hyperplasia and in-stent restenosis. The drug is gradually released to the surrounding tissue and the polymer coating is fully degraded over a predetermined time.

Figure 7:
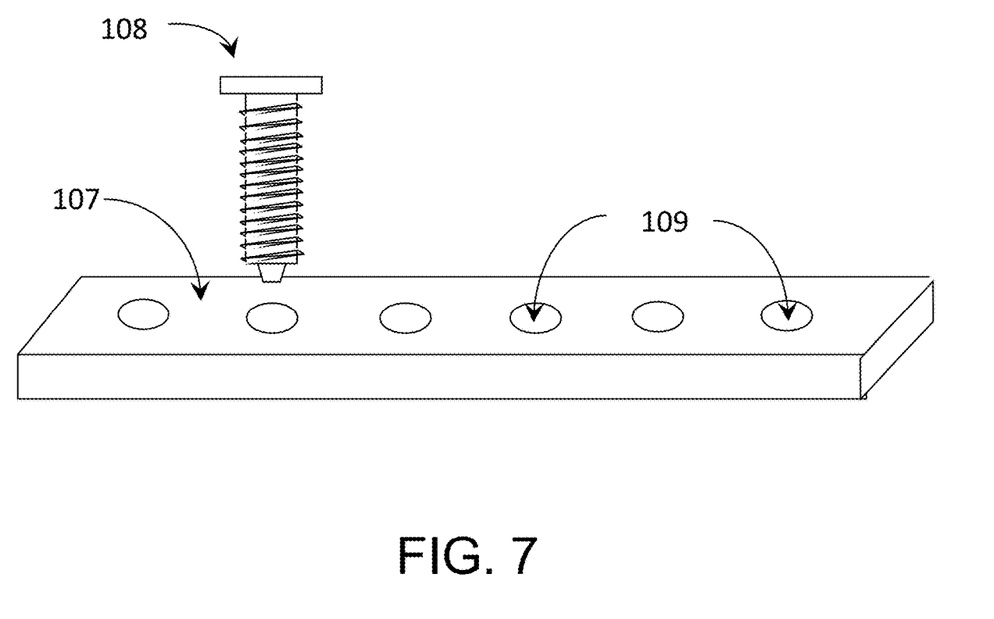
FIG. 7 is a top view of a bone plate and screw used to fix fractured bones.

The present inventions on the biodegradable metals can be used to fabricate orthopedic implants, for example but not limited to, bone plates 107 and screws 108 in FIG. 7 to fix and repair fractured bones. The bone fragments are repositioned into their normal alignment by the bone plates 107 and are attached together by the screws 107 through the holes 109 on the bone plate 107. The bone plate 107 and screws 108 in FIG. 7 shall be gradually degraded over a predetermined time after bone healing and thus it avoids the secondary surgery to remove the plate and screws.

Both the bone plate 107 and screws 108 have a layered composite structure as illustrated in FIGS. 1 and 2, comprising the iron layers 100 and alloying metallic layers 101. However, the iron layers 100 in the bone plate 106 could be significantly thicker than that in the exemplary small diameter tube 105. By way of example, but not limitation, the thickness of the iron layers 100 in the bone plates 107 can be up to 1 mm, while the thickness of alloying metallic layers 101 may remain in the range from 0.01 μm to 2 μm.

The fabrication processes of the implantable medical devices using the iron-based biodegradable metals in the present inventions include, but not limit to, laser cutting, laser welding, milling, drilling, turning, acid pickling, electropolishing, cleaning, passivation, and sterilization.

Although the invention disclosed herein has been described in terms of the preferred embodiments above, numerous modifications and/or additions to the above-described preferred embodiments would be readily apparent to one skilled in the art. By way of example, but not limitation, the invention includes any combination from the various alloying elements, composite structures, fabrication processes, and embodiments disclosed in the specification that are not already described. It is intended that the scope of the present invention extends to all such modifications and/or additions and that the scope of the present inventions is limited solely by the claims set forth below.

I claim:

1. An iron-based biodegradable medical implant comprising:
    A composite structure having a higher biodegradation rate than pure iron or pure zinc, said composite structure consisting of multiple iron layers alternating with alloy layers, wherein said iron layers have grain boundaries and have a thickness of 5 um to 1 mm and said alloy layers have a thickness of 0.01 um-2 um,
    said alloy layers comprising an alloying element wherein said alloying element is present in said composite structure in amounts less than 0.5% by weight and is selected from the group consisting of zinc, magnesium and combinations thereof;
    and wherein said iron-based biodegradable medical implant is selected from the group consisting of stents, orthopedic implants, surgical sutures, surgical staples, and reconstructive dental implants.

2. The iron-based biodegradable medical implant of claim 1 wherein:
    said iron layers comprises both large columnar iron grains and small equiaxed iron grains.

3. The iron-based biodegradable medical implant of claim 1 wherein said alloy layers and said grain boundaries comprise second-phase particles of iron oxides selected from the group consisting of ferric oxides and ferrous oxides.

4. The iron-based biodegradable medical implant of claim 1, wherein:
    said iron layers have identical thicknesses or different thicknesses.

5. The iron-based biodegradable medical implant of claim 1, wherein the orthopedic implant is a bone plate or a bone screw.

6. The iron-based biodegradable medical implant of claim 1 wherein said iron-based biodegradable medical implant is a surgical suture or surgical staple.

7. The iron-based biodegradable medical implant of claim 1 wherein said composite structure is made by an additive manufacturing technology selected from the group consisting of laser selective sintering, electron beam selective melting, physical vapor deposition, electroforming, electroplating, and friction stir processing.

8. The iron-based biodegradable medical implant of claim 1, wherein:
    said iron-based biodegradable medical implant is a stent which optionally comprises a biodegradable polymer coating with an anti-proliferative drug included therein.

9. The iron-based biodegradable medical implant of claim 8, wherein:
    said stent is made by laser cutting a tube consisting of said composite structure, wherein said tube has an outer diameter ranging from 1.20 mm to 5.00 mm and a wall thickness ranging from 0.04 mm to 0.25 mm.

10. The iron-based biodegradable medical implant of claim 9, wherein:
    said tube comprises multiple circular iron layers alternating with multiple circular alloy layers when viewed from the cross section of said tube, and said tube has a yield strength ranging from 150 MPa to 600 MPa.

11. The iron-based biodegradable medical implant of claim 9, wherein:
    said tube has an outer layer and an inner layer, wherein said outer and inner layers individually comprise either said iron layer or said alloy layer.

* * * * *